(12) United States Patent
Takasaki et al.

(10) Patent No.: US 7,828,021 B2
(45) Date of Patent: Nov. 9, 2010

(54) METHOD OF STORING (METH)ACRYLIC ESTER

(75) Inventors: Kenji Takasaki, Yokkaichi (JP); Shuhei Yada, Tokyo (JP); Yasushi Ogawa, Yokkaichi (JP); Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 1027 days.

(21) Appl. No.: 11/569,308

(22) PCT Filed: Nov. 5, 2004

(86) PCT No.: PCT/JP2004/016424

§ 371 (c)(1),
(2), (4) Date: Nov. 17, 2006

(87) PCT Pub. No.: WO2005/115967

PCT Pub. Date: Dec. 8, 2005

(65) Prior Publication Data

US 2008/0011385 A1    Jan. 17, 2008

(30) Foreign Application Priority Data

May 31, 2004   (JP)   .............................. 2004-160807

(51) Int. Cl.
  *B65B 1/20*   (2006.01)
(52) U.S. Cl. ......................................... 141/11; 562/532
(58) Field of Classification Search ............ 141/1, 141/2, 11, 69, 83, 98; 562/532
See application file for complete search history.

(56) References Cited

U.S. PATENT DOCUMENTS

| | | | |
|---|---|---|---|
| 4,260,821 A * | 4/1981 | Benjamin | ................... 562/532 |
| 4,873,217 A | 10/1989 | Kawajiri et al. | |
| 5,109,713 A * | 5/1992 | Romero et al. | ............ 73/864.83 |
| 5,993,687 A * | 11/1999 | Kishino et al. | .......... 252/182.14 |
| 6,265,495 B1 * | 7/2001 | Hirata et al. | ................. 525/404 |
| 6,376,703 B1 * | 4/2002 | Nagano | ....................... 560/205 |
| 6,900,275 B2 * | 5/2005 | Tomita et al. | ................ 525/404 |
| 2008/0041765 A1 * | 2/2008 | Larson et al. | ................ 208/134 |

FOREIGN PATENT DOCUMENTS

| | | |
|---|---|---|
| EP | 0279374 A1 | 8/1988 |
| JP | 2002 326976 | 11/2002 |
| JP | 2004 83460 | 3/2004 |
| JP | 2004-123169 | 4/2004 |
| RU | 1792344 A3 | 1/1993 |
| WO | 03 043969 | 5/2003 |
| WO | 03 057658 | 7/2003 |

OTHER PUBLICATIONS

Acrylic Acid and Acrylic Esters, "Safety Guidebook for Handling Acrylic Acid and Acrylic Esters (The 6th Edition)", The Japan Acrylic Ester Manufacturers Association (JAEM), 2002. (With Partial English Translation).

* cited by examiner

*Primary Examiner*—Timothy L Maust
(74) *Attorney, Agent, or Firm*—Oblon, Spivak, McClelland, Maier & Neustadt, L.L.P.

(57) ABSTRACT

A method of storing (meth)acrylate in a tank of a less expensive and highly versatile material without losing stability of the stored (meth)acrylate. To be specific, a method of storing (meth)acrylate in a tank, including supplying an appropriate gas for storing (meth)acrylate into the tank, in which: the tank is made of a carbon steel material; the gas has a water concentration of 100 ppm or less; and the (meth)acrylate has a (meth)acrylic acid concentration of 30 ppm or less.

18 Claims, No Drawings

METHOD OF STORING (METH)ACRYLIC ESTER

TECHNICAL FIELD

The present invention relates to a method of storing acrylate or methacrylate (which may also be collectively referred to as "(meth)acrylate"). The present invention more specifically relates to a method allowing long-term stable storage of (meth)acrylate in a tank of a less expensive carbon steel material.

BACKGROUND ART (Meth)acrylate is an easily polymerizable compound and a compound which compose an explosive composition at normal temperatures (compound possibly reaching a concentration within the explosive range at normal temperatures). Thus, when (meth)acrylate is stored in a storage facility, an oxygen concentration in an atmospheric gas of a gas phase portion in the storage facility must be controlled and a material of the storage facility must be selected carefully. For example, when a tank is used as the storage facility, an expensive stainless steel material such as SUS304 or SUS316 is generally recommended as a structural material thereof (see Non-Patent Document 1, for example).

Non-Patent Document 1: Safety Guidebook for Handling of Acrylic Acid and Acrylic Esters (6th edition): Japanese Acrylic Ester Manufacturer (JAEM)

DISCLOSURE OF THE INVENTION

Problem to Be Solved By the Invention

The present invention is aimed at storing (meth)acrylate in a storage facility of a less expensive and highly versatile material without losing stability of the (meth)acrylate during storage.

Means for Solving the Problem

The inventors of the present invention have conducted intensive studies on storing (meth)acrylate in relation to a material of a storage facility used for storing, conditions of a storage atmosphere, composition of the (meth)acrylate to be stored, and the like. As a result, the inventors of the present invention have found that (meth) acrylate can be stably stored for a long period of time in a tank of a carbon steel material by adjusting a water concentration in a gas supplied into the tank and a (meth)acrylic acid concentration in (meth)acrylate to be stored in the tank, and have completed the present invention.

That is, the present invention is described below.
(1) A method of storing (meth)acrylate in a tank, including supplying an appropriate gas for storing (meth)acrylate into the tank, in which: the tank is made of a carbon steel material; the gas has a water concentration of 100 vol ppm or less; and the (meth)acrylate has a (meth)acrylic acid concentration of 30 mass ppm or less.
(2) A method according to the item (1), in which the (meth)acrylate is methyl acrylate or ethyl acrylate.

In the specification of the present invention, a water concentration in a gas is represented in vol ppm and a (meth)acrylic acid concentration in (meth)acrylate is represented in mass ppm.

Effect of the Invention

A storage method of the present invention allows storing of (meth)acrylate in a tank of an inexpensive carbon steel material, thereby substantially reducing a cost for constructing a storage tank for (meth)acrylate.

BEST MODE FOR CARRYING OUT THE INVENTION

A storage method of the present invention is a method of storing (meth)acrylate having the following characteristics.
1. (Meth)acrylate is stored in a tank of an inexpensive carbon steel material.
2. (Meth)acrylate to be stored may contain a predetermined concentration of (meth)acrylic acid.
3. A gas having a specific composition is supplied to the tank.

The storage method of the present invention can be carried out in the same manner as that of a general storage method for (meth)acrylate as long as the above-mentioned characteristics are satisfied.

(Meth)acrylate to be stored with the method of the present invention may be an alkyl ester of acrylic acid or methacrylic acid. Examples of the alkyl ester include methyl ester, ethyl ester, butyl ester, isobutyl ester, tertiary butyl ester, 2-ethylhexyl ester, 2-hydroxyethyl ester, 2-hydroxypropyl ester, and methoxyethyl ester. Further, preferable examples of (meth)acrylate include methyl acrylate and ethyl acrylate. A solubility of water in lower alkyl (meth) acrylate is higher than a solubility of water in higher alkyl (meth)acrylate, and thus, more accurate adjustment of water content is required in storage of lower alkyl (meth)acrylate. Thus, the method of the present invention can be more preferably applied to a method of storing lower alkyl (meth)acrylate.

(Meth)acrylate to be stored with the method of the present invention may be (meth)acrylate obtained through esterification of (meth)acrylic acid with a conventional method.

In the method of the present invention, (meth)acrylate is stored in a tank.

The tank is supplied with a gas, and thus is preferably equipped with a gas blow tube for supplying the gas into the tank and a gas vent tube for venting the gas from the tank. Further, the tank may be provided with a circulation line (a liquid introduction tube, a liquid draw tube, and a line connecting the both tubes) for circulating a stored substance in the tank or with an stirrer for stirring the stored substance in the tank. Further, the tank may be provided with an arbitrary member as required.

A material of the tank can be arbitrarily selected from carbon steel materials. Examples of the carbon steel materials include: rolled steel for general structure specified in JIS G3101; and carbon steel for machine structural use specified in JIS G4051. The rolled steel for general structure preferably has a phosphorus content of 0.05 mass % or less and a sulfur content of 0.05 mass % or less, and examples thereof include SS400, SS490, and SS540. The carbon steel for machine structural use preferably has a carbon content of 0.08 to 0.61 mass %, a silicon content of 0.15 to 0.35 mass %, a manganese content of 0.3 to 0.9 mass %, a phosphorus content of 0.03 mass % or less, and a sulfur content of 0.035 mass % or less. An example thereof includes S45C.

As described above, the tank is preferably provided with a gas blow tube for supplying a gas into the tank and with a gas vent tube for venting a gas from the tank.

A gas to be supplied is an appropriate gas for storing (meth)acrylate in the tank. To be specific, the gas can suppress a polymerization reaction of (meth)acrylate in a gas phase portion and a liquid phase portion in the tank and prevent (meth)acrylate from composing an explosive composition. A predetermined oxygen concentration or more in the tank can suppress the polymerization reaction because a polymerization inhibitor (methoquinone, for example) added to (meth) acrylate stored in the tank functions more effectively. On the other hand, a predetermined oxygen concentration or less in the tank can prevent (meth)acrylate from composing an explosive composition. Thus, the gas to be supplied is a gas for adjusting an oxygen concentration in the gas phase portion and/or liquid phase portion in the tank.

The gas to be supplied into the tank is usually a mixed gas prepared by mixing a noncombustible inert gas (nitrogen, helium, neon, and argon (preferably nitrogen), for example) with molecular oxygen (may be oxygen in air). A concentration of molecular oxygen in the mixed gas is preferably 2 to 10 vol %, more preferably 5 to 8 vol %. If a concentration of molecular oxygen in the mixed gas is less than 2 vol %, the polymerization reaction may occur, and if a concentration thereof is more than 10 vol %, the explosive composition may be composed.

A gas to be supplied into the tank (preferably a mixed gas including molecular oxygen) has a water concentration of 100 ppm or less, preferably 10 to 100 ppm, and more preferably 50 to 100 ppm. The water concentration of 100 ppm or less can suppress corrosion of the tank (rust formation, for example) even when (meth) acrylate is stored in the tank which is made of a carbon steel material. On the other hand, a water concentration may be less than 10 ppm, which is a detection limit of GC analysis, but no cost-effectiveness can be expected even with a smaller water concentration than 10 ppm.

A water concentration in the gas to be supplied into a tank can be adjusted through any method of a cooling type, an absorption type, and an adsorption type using an adsorbent such as a molecular sieve, but is preferably adjusted using an air drier of an adsorption type.

Means for supplying a gas is not particularly limited as long as the means can supply a gas satisfying the above-mentioned limitation of oxygen concentration and water concentration. For example, air in the atmosphere may be supplied through an air drier or instrument air can be supplied through an air drier along with an inert gas.

The gas may be supplied to either the gas phase portion and/or liquid phase portion in the tank, but is preferably supplied to the liquid phase portion from the viewpoint of suppressing a polymerization reaction of (meth)acrylate.

(Meth)acrylate to be stored through the storage method of the present invention may contain a predetermined concentration of (meth)acrylic acid. The contained (meth)acrylic acid may be (meth)acrylic acid remained after production of (meth)acrylate through esterification of (meth)acrylic acid with alcohol. (Meth)acrylate has a (meth)acrylic acid concentration of 30 ppm or less, preferably 0.1 to 30 ppm, more preferably 0.1 to 10 ppm. A (meth)acrylic acid concentration of more than 30 ppm may cause corrosion of a carbon steel material as a tank material in long-term storage even when a water concentration in the gas to be supplied into the tank is properly adjusted. Further, a (meth)acrylic acid concentration may be less than 0.1 ppm, which is a detection limit of GC analysis, but no cost-effectiveness can be expected even with a smaller concentration than 0.1 ppm.

A (meth)acrylic acid concentration in (meth)acrylate to be stored can be controlled by appropriately adjusting a molar ratio of alcohol to (meth)acrylic acid in a reaction raw material, a reaction temperature, a water concentration in a reaction raw material, and the like in an esterification reaction for production of (meth)acrylate. To be specific, a (meth)acrylic acid concentration can be controlled by appropriately adjusting a ratio of (meth)acrylic acid to alcohol loaded into a reactor, a reaction temperature, and a residence time.

A (meth)acrylic acid concentration can also be controlled by purifying (including purifying through distillation) (meth)acrylate produced through the esterification reaction. To be specific, a (meth)acrylic acid concentration can be controlled by adjusting distillation temperature or a reflux ratio in a distillation column.

A substance stored with the storage method of the present invention may be one type of (meth)acrylate or may be a mixture of two or more types thereof. Further, the stored substance may be a mixture of (meth) acrylate and a compound except (meth) acrylate.

(Meth)acrylate to be stored with the storage method of the present invention is usually a composition mixed with a polymerization inhibitor. One type of the polymerization inhibitor may be used, or two or more types thereof may be used in combination.

Examples of the polymerization inhibitor include: phenol compounds such as hydroquinone and methoquinone (hydroquinone monomethyl ether); and phenothiazine compounds such as phenothiazine, bis-($\alpha$-methylbenzyl)phenothiazine, 3,7-dioctylphenothiazine, and bis-($\alpha$-dimethylbenzyl)phenothiazine. In particular, methoquinone can often be used.

The polymerization inhibitor may be dissolved in a solvent as required. The solvent is not particularly limited as long as the solvent can dissolve the polymerization inhibitor contained therein. For example, a phenol compound-based polymerization inhibitor such as hydroquinone or methoquinone dissolves in water, acetic acid, (meth)acrylic acid, (meth) acrylates, an aromatic compound, ketones, alcohols, or a mixed solvent of more than one type thereof, and such solvents are arbitrarily selected and used.

Further, methoquinone dissolves into (meth)acrylate. Thus, methoquinone can be used as a polymerization inhibitor for (meth)acrylate without using a solvent.

In the storage method of the present invention, a temperature of (meth)acrylate stored in the tank can be maintained at 15 to 50° C., preferably 15 to 30° C. The temperature can be maintained through any method. For example, when a circulation line is provided in the tank as described below, the temperature can be maintained by cooling at least part of (meth) acrylate drawn through a liquid draw tube with a heat exchanger and introducing the part into the tank through a liquid introduction tube.

In the storage method of the present invention, (meth) acrylate stored in the tank is preferably stored while being circulated to maintain a homogeneous mixed state of the polymerization inhibitor and (meth)acrylate in the tank. Thus, the tank is preferably provided with a liquid introduction tube, a liquid draw tube, and a line for directly connecting the both tubes. The circulation is preferably carried out rapidly for reducing accumulation of a liquid (including (meth) acrylate), which is a stored substance in the tank. To be specific, (meth)acrylate is preferably circulated at a liquid circulation time of 0.1 to 50 hours, preferably 0.2 to 30 hours obtained from the following equation (I).

Liquid circulation time (hours)=Liquid volume in tank (L)/Flow rate of circulating liquid (L/hour)　　Equation (I)

Further, in the storage method of the present invention, (meth) acrylate stored in the tank can be stored while being stirred. Thus, the tank may be provided with a stirrer. A stirrer having a stirring blade of a paddle type, a propeller type, and a turbine type may be used combined with a plate baffle or cylindrical baffle or the like as required.

Hereinafter, the present invention will be described in more detail by referring to examples, but the scope of the present invention is not limited by the examples.

EXAMPLE 1

Into a 2-L tank of SS400 equipped with a gas blow tube, a gas vent tube, and a stirrer, 1.5 L of ethyl acrylate having an acrylic acid concentration of 5 ppm was charged. While stirring ethyl acrylate at a stirring rate of 300 rpm, a mixed gas of instrument air and instrument nitrogen (adjusted to an oxygen concentration of 6%) was supplied into the tank through the gas blow tube after being passed through an air drier packed with activated alumina at 10 mL/min. A water concentration in the supply gas at an inlet of the tank was measured to be 60 ppm.

A temperature inside the tank was maintained at 25° C., and ethyl acrylate was continuously stored for 3 months. The tank was then opened for inspection of inside of the tank, and no rust formation was observed in the tank. Further, a purity of ethyl acrylate after the storage was measured, resulting in the same purity as that before the storage of 99.8 mass %.

COMPARATIVE EXAMPLE 1

The operation in Example 1 was repeated except that the air drier used in Example 1 was removed. A water concentration in a supply gas at an inlet of the tank was measured to be 500 ppm. After 3-month storage, the tank was opened for inspection thereinside, and spot-like rust_formation was observed in a vicinity of a gas-liquid interface on an inner surface of the tank. Further, a rust precipitate was observed in the liquid, and the liquid could not be used as a product.

COMPARATIVE EXAMPLE 2

The operation in Example 1 was repeated except that the acrylic acid concentration in ethyl acrylate used in Example 1 was changed to 50 ppm. After 3-month storage, the tank was opened for inspection thereinside, and spot-like rust formation was observed in a vicinity of a gas-liquid interface on an inner surface of the tank. Further, a rust precipitate was observed in the liquid, and the liquid could not be used as a product.

The invention claimed is:

1. A method of storing (meth)acrylate in a tank, comprising the steps of:
   supplying (meth)acrylate into the tank, and supplying a gas, which suppresses a polymerization reaction of (meth)acrylate in a gas phase portion and a liquid phase portion in the tank and prevents (meth)acrylate from composing an explosive composition, into the tank, wherein:
   the tank is made of a carbon steel material;
   the gas has a water concentration of 100 vol ppm or less; and
   the (meth)acrylate has a (meth)acrylic acid concentration of 30 mass ppm or less.

2. The method according to claim 1, wherein the (meth)acrylate comprises methyl acrylate or ethyl acrylate.

3. The method according to claim 1, wherein the carbon steel material is a rolled steel having a general structure specified in JIS G3101 or a carbon steel for machine structural use specified in JIS G4051.

4. The method according to claim 1, wherein the gas is a mixed gas prepared by mixing a noncombustible inert gas and molecular oxygen.

5. The method according to claim 4, wherein the concentration of molecular oxygen in the mixed gas is from 2 to 10 vol %.

6. The method according to claim 4, wherein the concentration of molecular oxygen in the mixed gas is from 5 to 8 vol %.

7. The method according to claim 1, wherein the water concentration is from 10 to 100 ppm.

8. The method according to claim 1, wherein the water concentration is from 50 to 100 ppm.

9. The method according to claim 1, wherein the gas is supplied to either a gas phase portion and/or liquid phase portion in the tank.

10. The method according to claim 9, wherein the gas is supplied to the liquid phase portion.

11. The method according to claim 1, wherein the (meth)acrylate has a methacrylic acid concentration of from 0.1 to 10 ppm.

12. The method according to claim 1, wherein the (meth)acrylate is stored as a composition mixed with a polymerization inhibitor.

13. The method according to claim 12, wherein the polymerization inhibitor comprises methoquinone.

14. The method according to claim 12, wherein the polymerization inhibitor is dissolved in a solvent.

15. The method according to claim 1, wherein the (meth)acrylate is stored in the tank at a temperature maintained at from 15 to 50° C.

16. The method according to claim 1, wherein the (meth)acrylate is stored in the tank at a temperature maintained at from 15 to 30° C.

17. The method according to claim 12, wherein the composition is stored while being circulated to maintain a homogeneous mixed state of the polymerization inhibitor and the (meth)acrylate in the tank.

18. The method according to claim 1, wherein the (meth)acrylate is stored in the tank while being stirred.

* * * * *